United States Patent [19]

Sweetin

[11] Patent Number: 4,637,805
[45] Date of Patent: Jan. 20, 1987

[54] APPARATUS AND METHODS FOR ENGAGING TOOTHPICKS TO ASSEMBLE A TOY STRUCTURE

[76] Inventor: Willard L. Sweetin, 5956 Fazon Rd., Bellingham, Wash. 98226

[21] Appl. No.: 681,871
[22] Filed: Dec. 14, 1984
[51] Int. Cl.$^4$ ............................................ A63H 33/10
[52] U.S. Cl. ..................................... 446/71; 403/172; 403/176; 446/126
[58] Field of Search .................... 446/85, 71, 124, 126; 403/171, 172, 174, 176, 178, 205, 403

[56] References Cited

U.S. PATENT DOCUMENTS

| | | | |
|---|---|---|---|
| 1,347,808 | 7/1920 | Franklin | 446/126 X |
| 1,764,226 | 6/1930 | Rennack | 403/171 |
| 3,939,581 | 2/1976 | Clarke | 446/124 X |

*Primary Examiner*—F. Barry Shay
*Attorney, Agent, or Firm*—Hughes & Cassidy

[57] ABSTRACT

Apparatus and methods are disclosed for engaging toothpicks to assemble a toy structure having different possible structural configurations. The toy structure is formed using toothpicks in conjunction with one or more support members, each support member including a plurality of support sleeves radiating outwardly therefrom. Each support sleeve has a conically shaped passageway therein for engaging one end of the toothpick wherein the support sleeve connects the toothpick to the support member. The toy structure is assembled by interconnecting the toothpicks with a plurality of support members. The support sleeves project outwardly in both the horizontal and vertical directions to provide support for toothpicks in the horizontal and vertical planes. The unattached end of a toothpick is "capped" with an additional support member having support sleeves thereon to act as sites for future expansion. The support sleeves may be angled to engage toothpicks between diagonally opposed support members which occupy the same plane. The diagonal support sleeves are sized to a predetermined length to allow the use of toothpicks having a uniform length within the structure. Toothpick locking means project into the sleeve passageway from the inner surface of the sleeve, the inward projection of the locking members terminating in a sharply defined ridge which penetrates into the surface of the toothpick when the toothpick is lodged within the sleeve.

18 Claims, 8 Drawing Figures

APPARATUS AND METHODS FOR ENGAGING TOOTHPICKS TO ASSEMBLE A TOY STRUCTURE

TECHNICAL FIELD

The present invention relates generally to apparatus and methods for engaging toothpicks to build toy structures in different configurations, and more particularly to apparatus and methods for using support members to engage and secure toothpicks in the horizontal and vertical planes in order to form a lattice-like structural framework.

BACKGROUND OF THE INVENTION

The manufacture of toys is a multibillion dollar industry which produces complex and sophisticated toys designed to interest the typical child who has grown up in an era surrounded by space travel, computer games, and television. Many of these modern day toys utilize sophisticated electronics and computer software resulting in significant expense to the purchaser.

Popular toys for younger children are the construction sets which may comprise not only simple building blocks used by very young children, but also more complex metal components which are assembled together using nuts and bolts, or molded plastic blocks which simply snap together. These construction sets have also increased greatly in price over the past few years generally due to the increase in cost of materials and labor. In addition, many of these construction sets are heavy and bulky, making it difficult for the child to carry, as well as making it difficult to pack with the child when travelling. Some of these building sets produce very large structures when assembled thereby requiring a substantial area for the child to play in.

There is needed, therefore, apparatus and methods for building toy structures which are relatively inexpensive, easy to transport and which can be assembled in a relatively small area.

SUMMARY OF THE INVENTION

Accordingly, it is a general aim of the present invention to provide improved apparatus and methods for engaging toothpicks to assemble toy structures in different configurations. Toothpicks are generally sold in bulk quantities and are quite inexpensive. Toothpicks are relatively thin and therefore can be densely packed; also they have sufficient longitudinal and lateral strength to provide structural integrity. In addition, the toothpick is a mass produced household item insuring its low cost and continuous availability.

Apparatus and methods for engaging toothpicks to assemble a toy structure comprise a support member having a plurality of sleeves which radiate outwardly therefrom. Each sleeve includes a conically shaped passageway for receiving the proximate end of a toothpick. The sleeve engages the toothpick thereby securing the toothpick to the support member in structure-like rigid relationship. The toy structure is assembled by interconnecting the toothpicks by means of a plurality of support members to form various structural configurations of the structure.

In one embodiment, the support sleeves radiate outwardly from the support member in both the horizontal and vertical planes in order to secure the toothpicks in horizontal and vertical structure-like relationships. The toy structure is formed by securing the toothpicks between adjacent support members which occupy the same plane. Expansion of the structure in either the horizontal or vertical planes is accomplished by interconnecting the toothpick with additional support members in the desired plane of expansion.

Another embodiment of the present invention includes diagonal support sleeves which radiate outwardly from the support member to secure toothpicks between diagonally located support members occupying the same plane.

The toothpicks are held in the support sleeves by toothpick locking members which project from the inner surface of the support sleeve along the majority of the length of the support sleeve. Each locking member defines an edge which penetrates into the surface of the toothpick when the toothpick is lodged in the sleeve passageway thereby providing an interference fit between the support sleeve and the toothpick.

BRIEF DESCRIPTION OF THE DRAWINGS

These and other objects and advantages of the present invention will become more readily apparent upon reading the following detailed description and upon reference to the attached drawings, in which.

Figure 1:
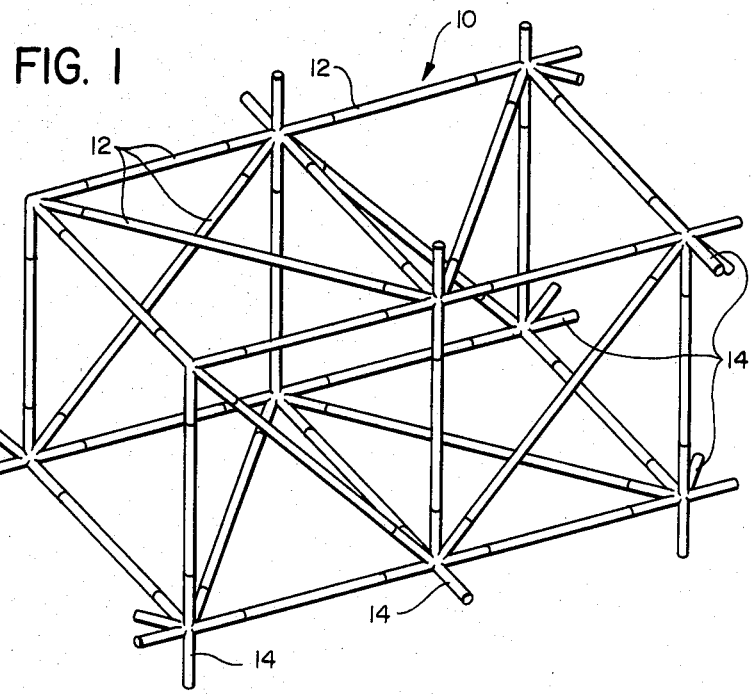
FIG. 1 is a perspective view of an exemplary toy structure.

While the present invention is susceptible of various modifications and alternative forms, specific embodiments thereof have been shown by way of example in the drawings and herein will be described in detail. It should be understood, however, that it is not intended to limit the invention to the particular forms disclosed, but, on the contrary, the intention is to cover all modifications, equivalents and alternatives falling within the spirit and scope of the invention as expressed in the appended claims.

DETAILED DESCRIPTION OF THE INVENTION

Figure 2:
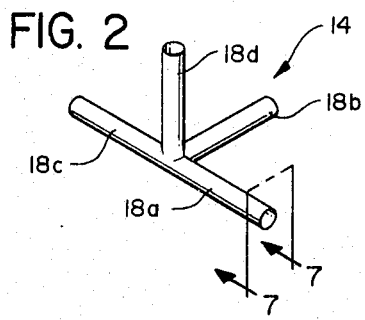
FIG. 2 is a perspective view showing a configuration of the support member for supporting toothpicks in two mutually perpendicular planes.

The present invention relates to apparatus and methods for engaging toothpicks to assemble a toy structure. Referring now to FIG. 1 there is shown an exemplary toy structure indicated at 10 comprising a plurality of toothpicks 12 held in a structure-like rigid relationship by support members 14. In FIG. 2 there is illustrated an exemplary configuration of support member 14 comprising support sleeves 18a through 18d which radiate outwardly in two mutually perpendicular planes to rigidly engage toothpicks 12 (FIG. 1). For clarity, the plane formed by support sleeve 18a, 18b and 18c in FIG. 2 will be referred to as the horizontal plane, whereas the plane formed by support sleeves 18b and 18d will be referred to as the vertical plane. It should be appreciated however, that the terms "horizontal" and "vertical" as applied to the present relationship of support sleeves 18a–d are merely relative to orientation of support member 14 in FIG. 2, an orientation which may change depending upon the manner in which support member 14 is used in assembly of toy structure 10.

Specifically, support sleeves 18a–d are configured as follows: support sleeves 18a and 18c lie in the horizontal plane in contiguous axial alignment radiating outwardly in opposite directions; support sleeve 18d lies in the vertical plane perpendicular to support sleeves 18a, 18c; and support sleeve 18b lies in the horizontal plane perpendicular to support sleeves 18a, 18c. The outwardly radiating support sleeves 18a–d act as corner supports for engaging toothpicks 12 in the vertical and horizontal planes to support a frame-like network of toothpicks 12 forming toy structure 10. Toy structure 10 may be expanded in the horizontal and/or vertical planes by inserting additional toothpicks in any unoccupied sleeve 18a–d lying in the desired plane of expansion. The unattached end of a toothpick 12 may be "capped" with an additional support member 14; the direction of further expansion determined by the configuration of the "capping" support member 14, i.e., the number and direction of radiating support sleeves 18 included in the "capping" support member 14.

Figure 3:
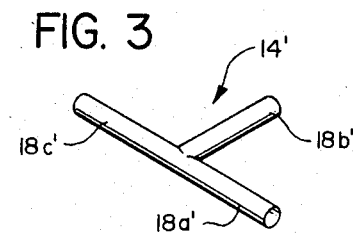
FIG. 3 is a perspective view showing a configuration of the support member for supporting toothpicks in one plane.

In order to provide variety to toy structure 10, support members 14 may be differently configured. For example, support member 14' illustrated in FIG. 3 comprises three outwardly radiating support sleeves 18a' through 18c'; sleeves 18a' and 18c' are in contiguous axial alignment but radiate outwardly in opposite directions in the horizontal plane; support sleeve 18b' radiates outwardly in the horizontal plane perpendicular to sleeves 18a' and 18c'. Support sleeves 18a' through 18c' are configured to receive toothpicks in only one plane, therefore support member 14' may be used to cap an exterior portion of toy structure 10 which requires a flat surface, such as for example, the bottom of toy structure 10 to allow interfacing with a floor or table (not shown).

Figure 4:
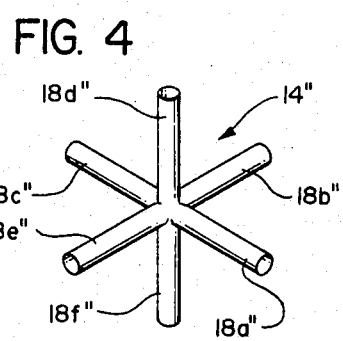
FIG. 4 is a perspective view showing a configuration of the support member for supporting toothpicks in two mutually perpendicular planes wherein each sleeve member is opposed by a contiguous axially aligned sleeve member radiating outwardly in the opposite direction.

Referring now to support member 14" in FIG. 4, there is shown six outwardly radiating support sleeves 18a" through 18f"; support sleeves 18a", 18c" are in contiguous axial alignment and radiate outwardly in opposite directions in the horizontal plane; support sleeves 18b", 18e" are in contiguous axial alignment and radiate outwardly in opposite directions in the horizontal plane perpendicular to support sleeves 18a", 18c"; and support sleeves 18d", 18f" are in contiguous axial alignment and radiate outwardly in opposite directions in the vertical plane. Support member 14" may be used as an interior corner support for toy structure 10; support sleeves 18a" through 18f" allow for expansion of toy structure 10 in any one of six possible directions.

Figure 5:
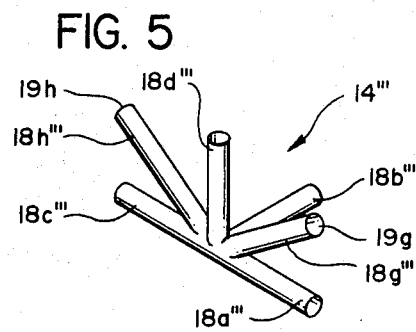
FIG. 5 is a perspective view showing a configuration of the support member for supporting toothpicks in two mutually perpendicular planes wherein additional transverse support is provided by diagonal support members.

In order to provide additional support to toy structure 10 as well as to make toy structure 10 more visually interesting and to make assembly thereof more challenging, there is shown in FIG. 5 diagonally located support sleeves 18g''', 18h''' which radiate outwardly in the vertical plane. Diagonal support sleeve 18g''' divides the angle formed by the convergence of support sleeves 18a''' and 18d'''. Diagonal support sleeve 18h''' divides the angle formed by the convergence of support sleeves 18c''' and 18d'''. Diagonal support sleeves 18g''' and 18h''' engage toothpick 12 to interconnect diagonally located support members 14 (FIG. 1) which lie in the same plane.

To allow the user to assemble toy structure 10 utilizing toothpicks of a uniform length, diagonal support sleeves 18g''', 18h''' are sized to a predetermined length. The length of diagonal support sleeves 18g''', 18h''' is defined as the distance from the center of support member 14''' to the respective outer ends 19g, 19h of support sleeves 18g''', 18h''', wherein the center of support member 14''' is defined as the intersection of support sleeves 18a''' through 18d'''.

Figure 6:
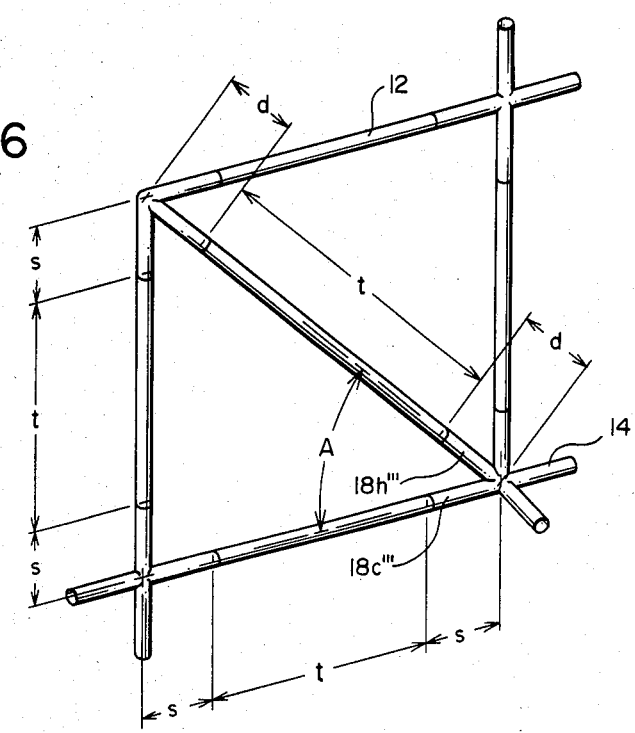
FIG. 6 is a perspective view of a portion of the toy structure illustrating the linear and angular relationships of the toothpicks and support sleeves.

Referring to FIG. 6 the length of support sleeves 18g''', 18h''' may be determined by the following relationship:

$$d = \frac{t + 2s}{2 \cos A} - \frac{t}{2}$$

wherein d=the length of the diagonal support sleeve 18g''', 18h''', t=the length of toothpick 12 minus the lengths of two end segments of toothpick 12 defined by the respective portions of toothpick 12 which are engaged by support sleeves 18, s=the length of support sleeve 18c''' as measured from the center of support member 14''' to the outward end of support sleeve 18c''', and A designates the angle formed by the convergence of diagonal support sleeve 18h''' and support sleeve 18c'''.

It should be appreciated that it is within the scope of this invention to locate the above described diagonal support sleeves 18g''', 18h''' in the horizontal plane as well as the vertical plane. Also, several configurations of support members 14 have been disclosed herein, however numerous other configurations of support member 14 are possible by varying both the number of support sleeves 18 as well as their angular relationships. Although the present invention has been described with reference to toothpicks of a single uniform length, the user may desire to assemble toy structure 10 with toothpicks of different lengths in order to add more variety to the assembly of toy structure 10 or to change its shape.

Figure 7:
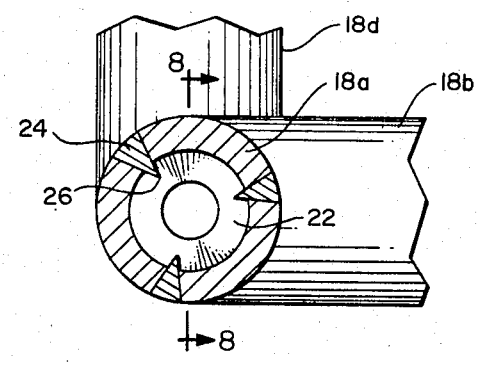
FIG. 7 is a sectional end view of the support member illustrated in FIG. 2.
Figure 8:
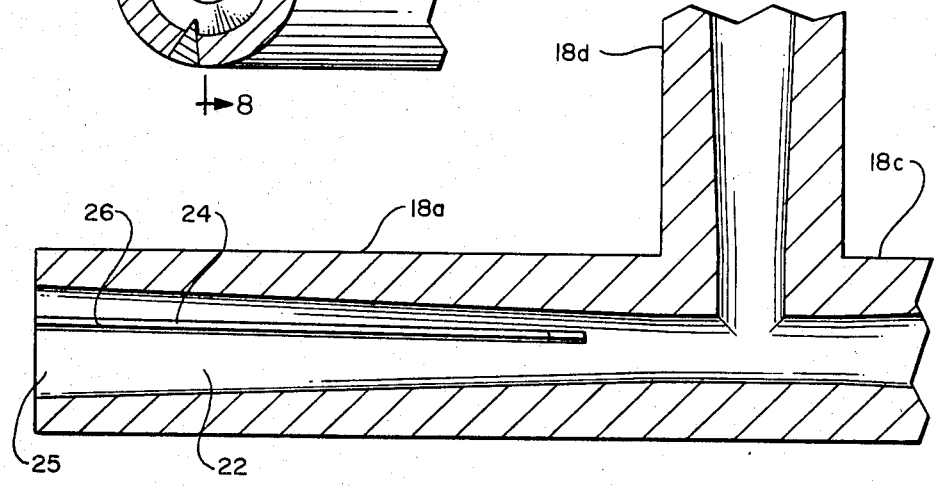
FIG. 8 is a sectional side view of the support member illustrated in FIG. 7.

In order to rigidly engage toothpick 12 within support sleeve 18, support sleeve 18 illustrated in FIGS. 7 and 8 includes a conically shaped passageway 22 for receiving the tapered end of a toothpick 12 therein. Toothpick 12 is held rigidly within passageway 22 by locking wedges 24 which project from the inner surface of sleeve 18 into passageway 22, and which extend longitudinally from mouth 25 of passageway 22 along the majority of the length thereof. Locking wedges 24 are positioned about the inner circumference of sleeve 18a at approximately 120° arcuate intervals; the projecting end of locking wedge 24 forming a sharply defined ridge 26 which penetrates into the surface of toothpick 12 when toothpick 12 is lodged in sleeve 18a.

What is claimed is:

1. Apparatus for engaging toothpicks to assemble a toy structure of multiple configurations, said apparatus comprising:

a. a support member including a plurality of support sleeves radiating outwardly therefrom, each of said support sleeves having a conically shaped passageway therein for engaging one of said toothpicks in a frictional fit therewith in proximity to an end of said toothpick, with each of said support sleeves connecting its said toothpick to said support member, whereby said toy structure is assembled by interconnecting said toothpicks with a plurality of said support members to form various structural configurations of said toy structure;

b. at least some of said support sleeves being horizontal support sleeves radiating outwardly from said support member in a horizontal plane to secure at least some of said toothpicks thereto in a horizontal structural relationship, said horizontal support sleeves being sized to a predetermined length to accommodate toothpicks of a uniform length within said structure, said horizontal support sleeves including:
   i. at least one first horizontal support sleeve for securing at least one of said toothpicks between adjacent support members which occupy said horizontal plane,
   ii. at least one second diagonal horizontal support sleeve for securing at least one of said toothpicks to diagonally located support members which occupy said horizontal plane, said second diagonal horizontal support sleeve having a lengthwise dimension which is greater than the lengthwise dimension of said first horizontal support sleeve to accommodate toothpicks of a uniform length in said toy structure;

c. at least some of said support sleeves being vertical support sleeves radiating outwardly from said support member in a vertical plane to secure at least some of said toothpicks thereto in a vertical structural relationship, said vertical support sleeves being sized to a predetermined length to accommodate toothpicks of a uniform length within said structure, said vertical support sleeves including:
   i. at least one first vertical support sleeve for securing at least one of said toothpicks between adjacent support members occupying said vertical plane;
   ii. at least one second diagonal vertical support sleeve for securing at least one of said toothpicks to diagonally located support members which occupy said vertical plane, said second diagonal vertical support sleeve sized to a predetermined length to accommodate toothpicks of uniform length in said toy structure;

d. the length of each second diagonal horizontal support sleeve as measured from a center of said support member to an end of said diagonal support sleeve being determined by the following relationship:

$$d = \frac{t + 2s}{2 \cos A} - \frac{t}{2}$$

wherein "d" is the length of said diagonal horizontal support sleeve, "s" is the length of said first horizontal support sleeve as measured from the center of said support member to an end of said first horizontal support sleeve, "t" is the length of said toothpick minus the length of two end segments of said toothpick defined by the locations where said toothpick is engaged by said support sleeves, and "A" is an angle formed by the convergence of said second diagonal horizontal support sleeve and said first horizontal support sleeve;

e. the length of said second diagonal vertical support sleeve as measured from the center of the support member to the end of said diagonal vertical support sleeve being determined by the following relationship:

$$d = \frac{t + 2s}{2 \cos A} - \frac{t}{2}$$

wherein "d" is the length of said diagonal vertical support sleeve, "s" is the length of said first vertical support sleeve as measured from the center of said support member to the outward end of said first vertical support sleeve, "t" is the length of said toothpick minus the lengths of two end segments of said toothpick defined by the locations where said toothpick is engaged by said support sleeves, and "A" is an angle formed by the convergence of said diagonal vertical support sleeve and said first vertical support sleeve.

2. A toy set comprising:
a. a plurality of toothpicks;
b. a plurality of support members for engaging said toothpicks to form a toy structure, each of said support members including a plurality of support sleeves radiating outwardly therefrom, each support sleeve having a passageway therein for engaging at least one of said toothpicks in a frictional fit therewith in proximity to an end of said toothpick, with said support sleeve connecting said toothpick to said support member, whereby said toy structure is assembled by interconnecting said toothpicks with said support members to form various structural configurations of said toy structure;

c. at least one of said support members comprising a plurality of horizontal support sleeves radiating outwardly from said support member in a horizontal plane to secure at least some of said toothpicks thereto in a horizontal structural relationship, said horizontal support sleeves sized to a predetermined length to accommodate toothpicks of a uniform length within said structure, said horizontal support sleeves including:
   i. at least one first horizontal support sleeve for securing at least one of said toothpicks between adjacent support members which occupy said horizontal plane,
   ii. at least one second diagonal horizontal support sleeve for securing at least one of said toothpicks to diagonally located support members which occupy said horizontal plane, said second diagonal horizontal support sleeve having a lengthwise dimension which is greater than the lengthwise dimension of said first horizontal support sleeve to accommodate toothpicks of a uniform length in said toy structure;

d. the length of each second diagonal horizontal support sleeve as measured from a center of said support member to an end of said diagonal support sleeve being determined by the following relationship:

$$d = \frac{t + 2s}{2 \cos A} - \frac{t}{2}$$

wherein "d" is the length of said diagonal horizontal support sleeve, "s" is the length of said first horizontal support sleeve as measured from the center of said support member to an end of said first horizontal support sleeve, "t" is the length of said toothpick minus the length of two end segments of said toothpick defined by the locations where said toothpick is engaged by said support sleeves, and "A" is an angle formed by the convergence of said second diagonal horizontal support sleeve and said first horizontal support sleeve;

e. at least one other of said support members being a second support member comprising vertical support sleeves radiating outwardly from said second support member in a vertical plane to secure at least some of said toothpicks thereto in a vertical structural relationship, said vertical support sleeves sized to a predetermined length to accommodate, toothpicks of a uniform length within said structure, said vertical support sleeves including:

i. at least one first vertical support sleeve for securing at least one of said toothpicks between adjacent support members occupying said vertical plane;

ii. at least one second diagonal vertical support sleeve for securing at least one of said toothpicks to diagonally located support members which occupy said vertical plane, said second diagonal vertical support sleeve sized to a predetermined length to accommodate toothpicks of uniform length in said toy structure;

f. the length of said second diagonal vertical support sleeve as measured from the center of the support member to the end of said diagonal vertical support sleeve being determined by the following relationship:

$$d = \frac{t + 2s}{2 \cos A} - \frac{t}{2}$$

wherein "d" is the length of said diagonal vertical support sleeve, "s" is the length of said first vertical support sleeve as measured from the center of said support member to the outward end of said first vertical support sleeve, "t" is the length of said toothpick minus the lengths of two end segments of said toothpick defined by the locations where said toothpick is engaged by said support sleeves, and "A" is an angle formed by the convergence of said diagonal vertical support sleeve and said first vertical support sleeve.

3. A support member for constructing a toy structure, wherein said support member is a first support member of a plurality of support members which comprise said toy structure, and where said toy structure comprises a plurality of elongate shafts of substantially equal length, where:

a. there are in addition to said first support member, at least two other support members, namely a second and third support member, said first, second and third support members being located at first, second and third juncture locations, respectively;

b. said first, second and third juncture locations being positioned relative to each other in a manner that an isoceles right triangle is formed by i) a first imaginary side line connecting said first juncture location with said second juncture location, ii) a second imaginary side line connecting said second juncture location with said third juncture location, and iii) a third imaginary hypotenuse line connecting said first juncture location with said third juncture location;

c. said shafts are arranged so that a first of said shafts extends between said first and second juncture locations along said first imaginary side line, a second of said shafts extends between said second and third juncture locations along said second imaginary side line, and a third of said shafts extends between said first and third juncture locations along said third imaginary hypotenuse line;

d. each of said shafts comprising a main middle section and two end connecting sections, the end sections of each shaft being connected to related ones of said support members;

said first support member comprising:

a. a first sleeve adapted to extend from said first junction location and to be positioned along said first imaginary side line between said first and second juncture locations;

b. a second sleeve rigidly connected to said first sleeve at a center location on said first support member and adapted to extend from said first juncture location and to be positioned along said third imaginary hypotenuse line between said first and third juncture locations under circumstances where said first sleeve extends from said first juncture location and along said first imaginary side line between said first and second juncture locations;

c. each sleeve having an outer end location and a shaft-receiving socket extending inwardly from the sleeve outer end location, with the socket being adapted to receive one of the end sections of a related one of said shafts;

d. the length of the second sleeve, as measured from the center location of the first support member to the outer end of said second sleeve, relative to the length of the first sleeve, as measured from the center location to the outer end of the first sleeve, being determined by the following relationship:

$$d = \frac{t + 2s}{2 \cos A} - \frac{t}{2}$$

wherein "d" is the length of the second sleeve, "s" is the length of the first sleeve, "t" is the length of the main middle section of each shaft, and "A" is an angle formed by alignment axes of the first and second sleeves.

4. The support member as recited in claim 3, wherein there is a third sleeve rigidly connected to said first and second sleeves, said third sleeve being aligned relative to said first and second sleeves in a manner that said third sleeve is perpendicular to a plane containing said first and second sleeves.

5. The support member as recited in claim 4, wherein there is a fourth support sleeve which is rigidly connected to said first and second sleeves and lying in a common plane with said first and second sleeves, said fourth sleeve having an alignment axis which is perpendicular to said first sleeve.

6. The support member as recited in claim 3, wherein there is a third sleeve rigidly connected to said first and second sleeves, and said third sleeve lies in a common plane with said first and second sleeves, said third sleeve having an alignment axis perpendicular to said first sleeve.

7. The support member as recited in claim 3, wherein there is:
   a. a third sleeve rigidly connected to said first and second sleeves, said third sleeve being aligned relative to said first and second sleeves in a manner that said third sleeve is perpendicular to a plane containing said first and second sleeves;
   b. a fourth sleeve which is rigidly connected to said first and second sleeves and lying in a common plane with said first and second sleeves, said fourth sleeve having an alignment axis which is perpendicular to said first sleeve;
   c. a fifth sleeve rigidly connected to said first, second, third and fourth sleeves, said fifth sleeve having an alignment axis parallel to said first sleeve.

8. The support member as recited in claim 3, wherein the socket defined by each sleeve is a tapered socket which tapers inwardly from the end of each sleeve.

9. The support member as recited in claim 3, wherein the socket of each sleeve comprises edge locking members extending into said socket to engage the end section of the related shaft.

10. The support member as recited in claim 9, wherein there is a plurality of said edge members extending inwardly into the socket of each sleeve.

11. A toy support structure comprising:
   a. at least three support members, namely a first, second and third support member located at first, second and third juncture locations, respectively;
   b. said first, second and third juncture locations being positioned relative to each other in a manner that an isoceles right triangle is formed by i) a first imaginary side line connecting said first juncture location with said second juncture location, ii) a second imaginary side line connecting said second juncture location with said third juncture location, and iii) a third imaginary hypotenuse line connecting said first juncture location with said third juncture location;
   c. a plurality of elongate shafts of equal length are arranged so that a first of said shafts extends between said first and second juncture locations along said first imaginary side line, a second of said shafts extends between said second and third juncture locations along said second imaginary side line, and a third of said shafts extends between said first and third juncture locations along said third imaginary hypotenuse line;
   d. each of said shafts comprising a main middle section and two end connecting sections, the end sections of each shaft being connected to related ones of said support members;
   e. said first support member comprising:
      i. a first sleeve adapted to be positioned along said first imaginary side line between said first and second juncture locations;
      ii. a second sleeve rigidly connected to said first sleeve at a center location on said first support member and adapted to be positioned along said third imaginary hypotenuse line between said first and third juncture locations under circumstances where said first sleeve extends along said first imaginary side line between said first and second juncture locations;
      iii. each sleeve having an outer end location and a shaft-receiving socket extending inwardly from the sleeve outer end location, with the socket being adapted to receive one of the end sections of a related one of said shafts;
      iv. the length of the second sleeve, as measured from the center location of the first support member to the outer end of said second sleeve, relative to the length of the first sleeve, as measured from the center location to the outer end of the first sleeve, being determined by the following relationship:

$$d = \frac{t + 2s}{2 \cos A} - \frac{t}{2}$$

wherein "d" is the length of the second sleeve, "s" is the length of the first sleeve, "t" is the length of the main middle section of each shaft, and "A" is an angle formed by alignment axes of the first and second sleeves;
   f. said third support member comprising:
      i. a third sleeve adapted to extend along said second imaginary side line between said third and second juncture locations;
      ii. a fourth sleeve rigidly connected to said third sleeve at a center location on said third support member and adapted to extend along said third imaginary hypotenuse line between said third and first juncture locations under circumstances where said third sleeve extends along said second imaginary side line between said third and second juncture locations;
      iii. each of said third and fourth sleeves having an outer end location and a shaft-receiving socket extending inwardly from the sleeve outer end location, with the socket being adapted to receive one of the end sections of a related one of said shafts;
      iv. the length of the fourth sleeve, as measured from the center location of the third support member to the outer end of the fourth sleeve, relative to the length of the third sleeve, as measured from the center location of the third support member to the outer end of the third sleeve, being determined by the following relationship:

$$d = \frac{t + 2s}{2 \cos A} - \frac{t}{2}$$

wherein "d" is the length of the fourth sleeve, "s" is the length of the third sleeve, "t" is the length of the main middle section of each shaft, and "A" is an angle formed by alignment axes of the third and fourth sleeves.

12. The structure as recited in claim 11, wherein there is a fifth sleeve rigidly connected to said first and second sleeves, said fifth sleeve being aligned relative to said first and second sleeves in a manner that said fifth sleeve is perpendicular to a plane containing said first and second sleeves.

13. The structure as recited in claim 12, wherein there is a sixth support sleeve which is rigidly connected to said first and second sleeves and lying in a common plane with said first and second sleeves, said sixth sleeve having an alignment axis which is perpendicular to said first sleeve.

14. The structure as recited in claim 11, wherein there is a fifth sleeve rigidly connected to said first and second sleeves, and said fifth sleeve lies in a common plane with said first and second sleeves, said fifth sleeve having an alignment axis perpendicular to said first sleeve.

15. The structure as recited in claim 11, wherein there is:
   a. a fifth sleeve rigidly connected to said first and second sleeves, said fifth sleeve being aligned relative to said first and second sleeves in a manner that said fifth sleeve is perpendicular to a plane containing said first and second sleeves;
   b. a sixth sleeve which is rigidly connected to said first and second sleeves and lying in a common plane with said first and second sleeves, said sixth sleeve having an alignment axis which is perpendicular to said first sleeve;
   c. a seventh sleeve rigidly connected to said first, second, fifth and sixth sleeves, said seventh sleeve having an alignment axis parallel to said first sleeve.

16. The structure as recited in claim 11, wherein the socket defined by each sleeve is a tapered socket which tapers inwardly from the end of each sleeve.

17. The structure as recited in claim 11, wherein the socket of each sleeve comprises edge locking members extending into said socket to engage the end section of the related shaft.

18. The structure as recited in claim 17, wherein there is a plurality of said edge members extending inwardly into the socket of each sleeve.

* * * * *